US00PP10059P

United States Patent [19]

Hill, Jr.

[11] Patent Number: Plant 10,059

[45] Date of Patent: Oct. 7, 1997

[54] GUZMANIA PLANT NAMED FIREWORKS

[75] Inventor: Herbert H. Hill, Jr., Lithia, Fla.

[73] Assignee: Twyford International, Inc., Santa Paula, Calif.

[21] Appl. No.: 651,714

[22] Filed: May 22, 1996

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new cultivar of Guzmania named 'Fireworks' having large star shaped, long lasting, dark red inflorescence with yellow-green terminal bracts and branch spikes. The foliage is durable and resistant to tip browning. Plants of 'Fireworks' tolerate a wide range of cultural conditions and are easy to grow.

2 Drawing Sheets

The present invention relates to a new and distinct cultivar of Guzmania, a genus within the family bromeliaceae, hereinafer referred to by the cultivar name 'Fireworks'. The new cultivar is a hybrid resulting from a cross identified below.

Guzmania comprise a genus of over 100 species of herbaceous evergreen perennials suitable for cultivation in the home or under glass. Guzmania are predominantly epiphytic with a few terrestrial species, and are native to the tropics. For the most part, the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania is generally from yellow through orange but may also include flame red and red-purple. White or yellow, tubular, three petalled flowers may also appear on a stem or within the leaf rosette but are usually short lived.

Guzmania may be advantageously grown as potted plants for greenhouse or home use. Desirably, the plants are shaded from direct sunlight, and during the spring to autumn period, the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequenntly done through the use of tissue culture practices. Propagation can also be from off-shoots produced by the plant which may then be rooted. The resulting off-shoots are detached from the mother plant and may be grown in an appropriate soil or bark mixture. Many types are propagated relatively uniformly from seeds.

The new cultivar 'Fireworks' is the product of a planned breeding program and was originated by the inventor Herbert H. Hill Jr. from a cross made during such program in Lithia, Fla. in 1987. The male or pollen parent was a plant resulting from a cross of *G. memoria* and *G. maagnifica*. The female, or seed parent was a presently unknown cultivar of *Guzmania squarrosa*.

The new cultivar was selected from the progeny of the stated cross after commencement of flowering in 1991. Subsequent asexual propagation by off-shoots by the inventor in Lithia, Fla. has demonstrated that the combination of characteristics as herein disclosed for the new cultivar 'Fireworks' are firmly fixed and are retained through successive generations of asexual reproduction.

'Fireworks' is particularly characterized by the following:

1. The inflorescence produced by 'Fireworks' has dark red primary bracts, and contrasting yellow-green terminal bracts and branch spikes.

2. The foliage of 'Fireworks' is dark olive green, and is resistant to leaf tip browning and leaf spotting. The foliage is leathery and resistant to damage from handling and shipping.

3. Plants of 'Fireworks' tolerate temperature extremes from 38°–94° F. without noticeable damage.

4. Plants of 'Fireworks' tolerate a wide range of cultural conditions, and are easy to grow.

Perhaps the closest comparison cultivar is Guzmania 'Triumph', disclosed in U.S. Plant Pat. No. 8,656 are characterized by its long lasting, bright red inflorescence. The floral bracts of 'Fireworks' are a darker red, and longer than those of 'Triumph'. The branch spikes and terminal bracts of 'Fireworks' are yellow-green, those of 'Triumph' are red tipped with white. The inflorescence of 'Triumph' is compact and cone shaped, compared to the wide and star shaped inflorescence of 'Fireworks'. Plants of 'Fireworks' are larger, having longer leaves than those of 'Triumph'.

Guzmania 'Fireworks' has not been tested under all available environmental conditions. The phenotype may vary with variations in environmental conditions such as temperature, light intensity, day length and humidity without, however, any variance in genotype.

The accompanying color photographic drawings show typical characteristics of 'Fireworks', with colors being as true as possible with illustrations of this type.

The photo on sheet 1 is of a 14 month old plant of 'Fireworks' grown from an off-shoot, and finished in a 10.2 cm pot.

The photo on sheet 2 is a close up view showing in more detail the inflorescence of the plant of 'Fireworks' shown in the photo on sheet 1.

The following description is taken from the plant illustrated in the photos on sheets 1 and 2. The plant was grown in Lithia, Fla. by the inventor under greenhouse conditions which are typical of the industry. Color references are made to The Royal Horticultural Society Colour Chart (R.H.S.).

I. Plant:

*Form and growth habit.*—Basal Rosette of closely layered strap-like leaves arranged around a short central stem.

*Height.*—Approximately 38 cm–40 cm including inflorescence.

*Diameter.*—Approximately 83 cm–88 cm.

II. Foliage:

*Size of leaf.*—The basal leaves are approximately 53 cm–58 cm long, and 4.9 cm–5.5 cm wide (flattened).

At their widest point near the base, the leaves are approximately 10.0 cm to 11.2 cm wide.

*Shape of leaf.*—The leaf blade is ligulate with an acute tip. The leaf blade is channeled. The margins are entire. The leaves are curved outward over their length.

*Surface texture.*—The leaf blade is stiff and leathery, with a glossy surface.

*Color.*—The leaves are dark green throughout the foliage. The adaxial surface is much darker and greener than but closest to 137 A, and the abaxial surface is much darker and greener than but closest to 147 B. The leaf margins are bordered and occasionally flushed with 187 C near their base.

*Average number of leaves.*—The plant produces approximately 17 leaves before producing an inflorescence.

*Roots.*—Roots are white, changing to brown, wiry with fine laterals.

III. Bracts:

*Size and color.*—The upper and most brilliantly colored (primary) bracts are approximately 7.3 cm–15 cm long, and approximately 3.2 cm to 4.0 cm wide. The adaxial and abaxial surfaces are 45 A in color. The tips of the bracts are dark anthocyanous 183 A in color. The most apical and reduced terminal bracts (those enclosing flowers, and buds) are 4.1 cm–4.7 cm long, 0.9 cm–2.0 cm wide. The adaxial and abaxial surfaces are 150 C and 151 A respectively, in color, occasionally flecked with 185 A near the tip. The scape bracts are approximately 17.5 cm to 36.2 cm long, and approximately 2.5 cm to 5.7 cm wide. The scape bracts diminish in length and become more brightly colored ascending the scape. The adaxial surface is darker and greener than, but closest to 137 A, with 184 A-B blotches and striations. The area covered with 184 A-B increases on the upper scape bracts. The abaxial surface is greener than but closest to 147 B, with 184 A-B blotches and striations covering the lower ⅔ of the bract.

*General shape and arrangement.*—The bracts are ligulate with acute tips, arranged in closely spaced vertical ranks along the inflorescence. The scape bracts have an internode space approximately 16 mm–20 mm along the scape. The uppermost terminal and primary bracts are very closely spaced (1.0 mm–9.0 mm) apart. The inflorescence is approximately 18 cm to 20 cm in width.

*Number.*—Terminal bracts, approximately 33; primary bracts, approximately 20; scape bracts, approximately 7.

*Texture.*—Leathery, with a glossy surface.

*Margin.*—Entire.

*Scape.*—The scape is approximately 35 cm tall, approximately 11 mm to 13 mm in diameter, and 145 B-C in color.

IV. Branch spikes: The terminal end of the inflorescence contains approximately 5 branch spikes which protrude from under the primary bracts, each containing approximately 15 flowers. The bracts of the branch spikes are approximately 4.4 cm long, 1.0 cm wide, and 150 C to 151 A in color.

V. Flowers:

*Borne.*—Terminal in the inflorescence, and in branch spikes.

*Individual flowers.*—Approximately 25 flowers or flower buds present, terminal in the inflorescence and concealed under bracts. The calyx is gamosepalous, three sepals, each 2.2 cm long, lighter than, but closest to 150 D to 155 D in color. The corolla is gameopetalous, three petals each 4.7 cm long and yellow 16 B in color.

*Time of blooming.*—In mature plants, flowering begins approximately 12–14 weeks after induction, at any time of the year.

*Duration of inflorescence.*—The inflorescence will hold its color approximately 6–8 months. Individual flowers last 1 day, and the total duration of flowering is about 12 weeks.

VI. Reproductive organs:

*Ovary.*—Superior, three locules, 10 mm long, 145 D in color.

*Style.*—3.2 cm long, 150 D in color, 150 B at tip.

*Stamens.*—Six present, filament 3.4 cm long, aanthers 5 mm long, 161 D in color.

VII. Seed characteristics: Steerile F1 hybrid.

It is claimed:

1. A new and distinct cultivar of Guzmania plant named 'Fireworks', as illustrated and described.

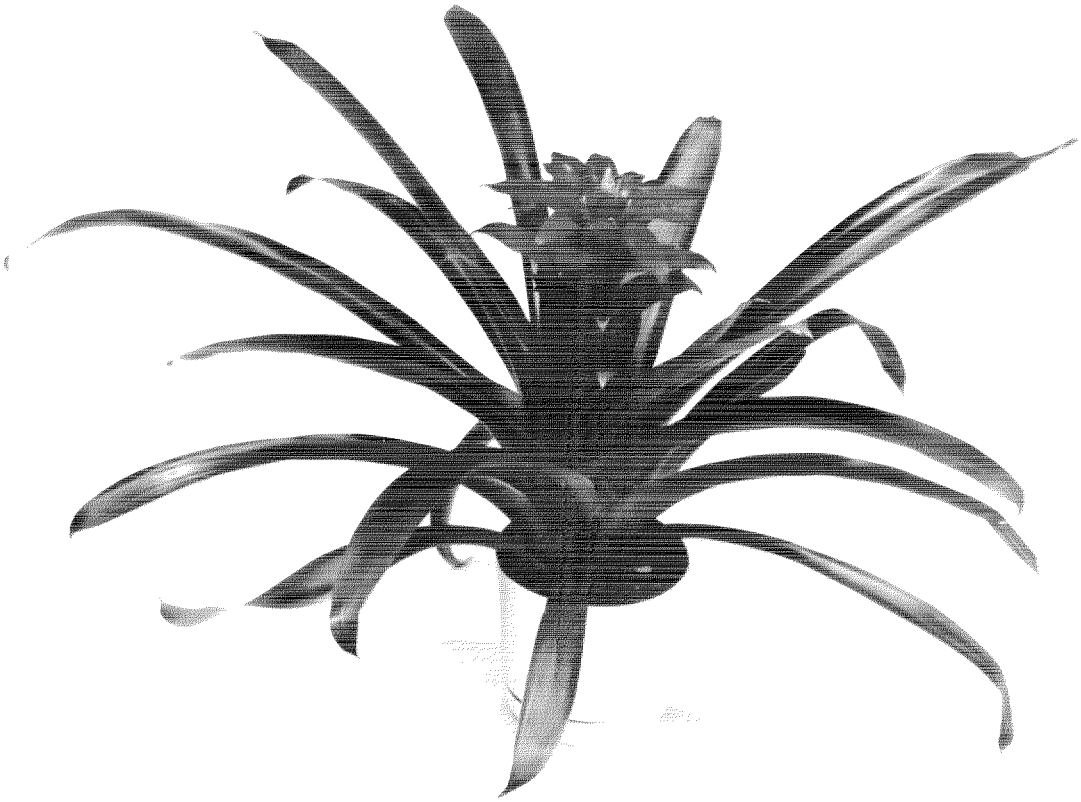

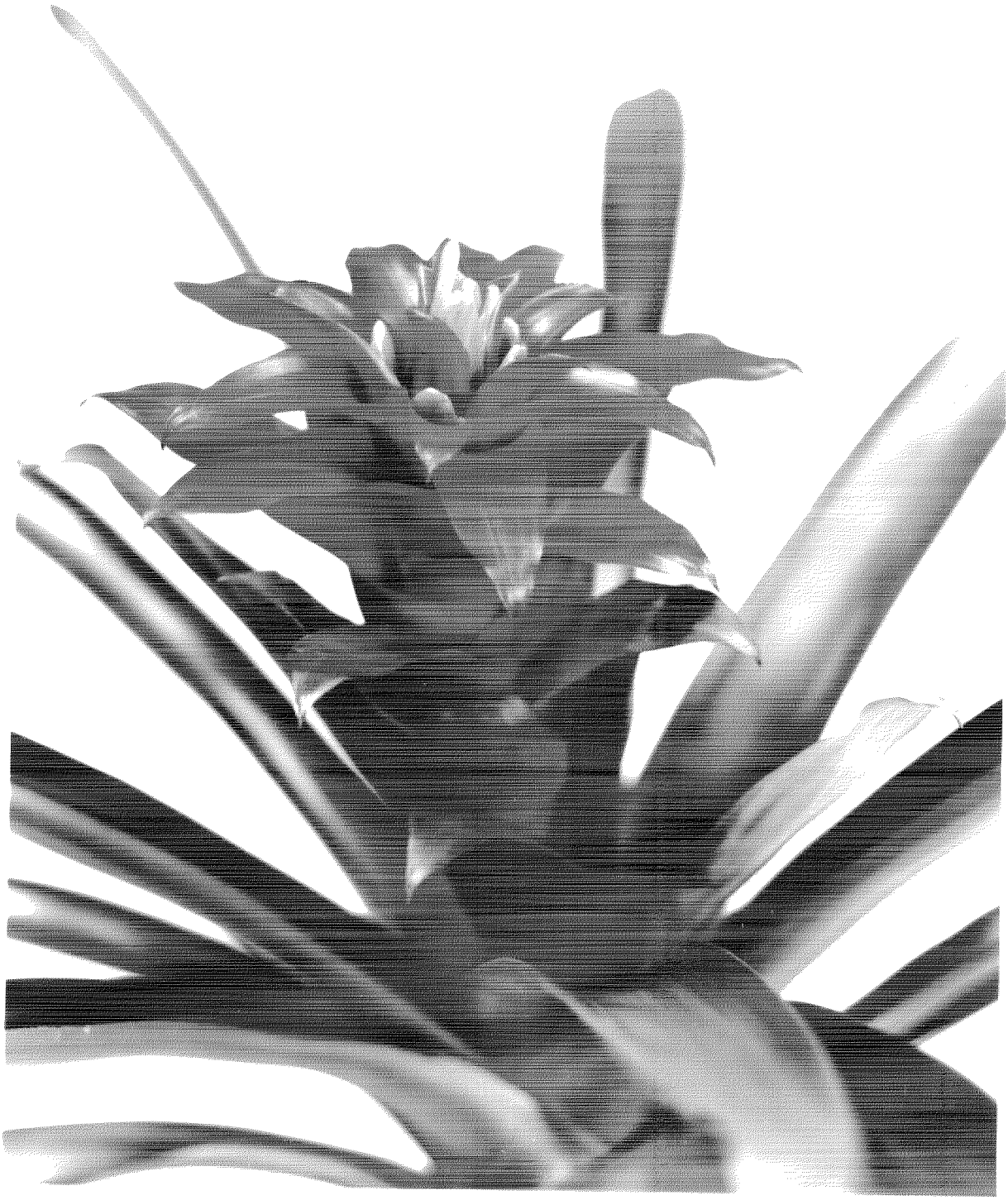

* * * * *